(12) United States Patent
Uphade et al.

(10) Patent No.: US 8,252,710 B2
(45) Date of Patent: Aug. 28, 2012

(54) ZEOLITE-BINDER CATALYST COMPOSITION

(75) Inventors: Balu Shivaji Uphade, Pune (IN); Srikant Gopal, Pune (IN)

(73) Assignee: Saudi Basic Industries Corporation, Riyadh (SA)

( * ) Notice: Subject to any disclaimer, the term of this patent is extended or adjusted under 35 U.S.C. 154(b) by 444 days.

(21) Appl. No.: 12/448,738

(22) PCT Filed: Dec. 5, 2007

(86) PCT No.: PCT/EP2007/010763
§ 371 (c)(1),
(2), (4) Date: Aug. 21, 2009

(87) PCT Pub. No.: WO2008/080517
PCT Pub. Date: Jul. 10, 2008

(65) Prior Publication Data
US 2010/0029999 A1    Feb. 4, 2010

(30) Foreign Application Priority Data

Jan. 3, 2007 (IN) .......................... 0026/DEL/2007

(51) Int. Cl.
*B01J 29/06* (2006.01)
*C07C 15/00* (2006.01)

(52) U.S. Cl. ............. 502/61; 502/63; 502/64; 502/65; 502/66; 585/407

(58) Field of Classification Search ............ 502/61, 502/63, 64, 65, 68; 585/407
See application file for complete search history.

(56) References Cited

U.S. PATENT DOCUMENTS

| 4,482,531 A * | 11/1984 | Kuehl ........................... 423/706 |
| 4,508,839 A * | 4/1985 | Zandona et al. ................. 502/65 |
| 4,629,818 A | 12/1986 | Burress |
| 4,855,522 A | 8/1989 | Diaz |
| 5,173,463 A | 12/1992 | Macedo |
| 5,248,642 A | 9/1993 | Kumar et al. |
| 5,382,742 A * | 1/1995 | Morrison et al. .............. 585/654 |
| 6,255,243 B1 | 7/2001 | Drake et al. |
| 2002/0036284 A1 * | 3/2002 | Speronello et al. ...... 252/187.21 |

FOREIGN PATENT DOCUMENTS

| EP | 0 130 251 B1 | 1/1985 |
| EP | 0 201 152 A2 | 11/1986 |

OTHER PUBLICATIONS

Choudhary et al., "Influence of binder on the acidity and performance of H-Gallosilicate (MFI) zeolite in propane aromatization", Applied Catalysis A: General 162 (1997) 223-233.*
International Search Report: International Application No. PCT/EP2007/010763; International Filing Date: Dec. 12, 2007; Date of Mailing: Jun. 3, 2008; 4 Pages.
Written Opinion of the International Searching Authority; International Application No. PCT/EP2007/010763; International Filing Date: Dec. 5, 2007; Date of Mailing: Jun. 3, 2008; 4 Pages.
Meier, W M & Olson D H; Atlas of Zeolite Framework Types, Fifth Revised Edition, p. 3-18; Butterworth-Heineman, Boston, MA.
Choudhary,V.R.; Influence of catalyst binder in acidity activity/selectivity of Ga/H-ZSM-5 zeolite in propane aromatization;Prod Indian Acad Sci(ChemSci);Oct. 1999; p. 669-676; v111.
Kirk-Othmer Encyclopaedia of Chemical Tech; 4th Ed., vol. 16; John Wiley & Sons, New York.
Meier, W M & Olson D H; Atlas of Zeolite Framework Types, Fifth Revised Edition, p. 3-18; Butterworth-Heineman, Boston, MA, 2001.

* cited by examiner

*Primary Examiner* — Elizabeth Wood
(74) *Attorney, Agent, or Firm* — Cantor Colburn LLP

(57) ABSTRACT

Catalyst composition comprising a zeolite and a binder, wherein the zeolite is a Ga containing zeolite and the binder is a La modified kaolin and process for converting lower alkanes to aromatic hydrocarbons, using said catalyst composition. Preferably the aromatic hydrocarbons consist of at least 45 wt % of benzene, toluene and xylenes.

20 Claims, No Drawings

ZEOLITE-BINDER CATALYST COMPOSITION

The invention relates to a catalyst composition comprising a zeolite and a binder.

Bonded, or supported, zeolite catalysts are known to be useful as catalyst in the conversion of lower alkanes to aromatic hydrocarbons.

U.S. Pat. No. 4,855,522 discloses a zeolite based catalyst, containing a rare earth metal and optionally bonded with a suitable binder. Alumina and silica are mentioned as examples of such binders. The use of La modified kaolin as a binder is not mentioned.

U.S. Pat. No. 6,255,243 discloses a catalyst composition comprising a zeolite and a clay and optionally a compound which is called 'promoter'. It teaches that any clay can be used. As promoter elements from 9 groups of the periodic Table are mentioned, including rare earths. A promoter is said to be any compound that can suppress coke formation or enhance olefin production. Conversion rates reported are rather low.

In publication Proc. Indian Acad. Sci, (Chem. Sci.), Vol. III, No. 5, October 1999, pp. 669-676 it is shown that the use of kaolin as a binder produces a catalyst composition having considerably lower conversion rate of propane into aromatic hydrocarbons than alumina.

Object of the present invention is to provide a zeolite-binder catalyst composition that has a good alkane conversion and a good overall yield of aromatic hydrocarbons.

This object is achieved according to the invention in that zeolite is a Ga containing zeolite the binder is a La modified kaolin.

The catalyst composition according to the invention having the combination of a Ga containing zeolite and a La modified kaolin was found to show a higher alkane conversion and higher aromatics yield than compositions containing other binders, as such or rare-earth modified. It also shows a lower deactivation rate that the known Ga and La containing zeolite-binder catalysts.

Any commercially available zeolite which can catalyze the conversion of an alkane to an aromatic compound can be employed as the zeolite in the present invention. Examples of suitable zeolites include, but are not limited to, those disclosed in Kirk-Othmer Encyclopaedia of Chemical Technology, third edition, volume 15 (John Wiley & Sons, New York, 1991) and in W. M. Meier and D. H. Olson, "Atlas of Zeolite Structure Types," pages 138-139 (Butterworth-Heineman, Boston, Mass., 3rd ed. 1992). Optionally a zeolite or the catalyst composition can be steam treated before using the present invention. It is known to acid treat a zeolite before use in a catalyst composition but it appeared that the catalyst according to the present invention performs better when the zeolite has not been acid treated.

The presently preferred zeolites are those having medium pore sizes. ZSM-5 and similar zeolites that have been identified as having a framework topology identified as MFI are particularly preferred because of their shape selectivity.

The zeolite contains gallium. For the preparation of Ga containing zeolites the commonly known techniques in the art can be applied. Contacting the zeolite with a heated aqueous solution of a Ga salt e.g. gallium nitrate under continuous stirring has proven to be an effective method. Typically, the amount of Ga on the zeolite can range from 0.2 to 2.0 wt. %. The preferred range is 0.5 to 1.5 wt. %; most preferred range is 0.75 to 1.25 wt. %. It was found that in the catalyst according to the invention the amount of Ga can be lower than 1 wt %, preferably lower than 0.95 wt %.

The binder is La modified kaolin. Kaolin is known per se and all known varieties can be used in the catalyst of the present invention. For the modification of kaolin with a metal several methods are known in the art. An effective method comprises contacting the kaolin with a heated aqueous solution of a La salt under continuous stirring. After filtering and drying the La modified kaolin preferably is calcined by exposing it during typically 1-10 hours to a moisture-free air flow at a temperature between 500 and 800° C. Lanthanum was found to be the most effective rare earth metal for the purpose of the invention. Alternatively, the as-synthesized and dried La modified kaolin can be used as such without further treatments as a binder for aromatization catalyst. In some embodiments, the kaolin has not been acid treated.

The catalyst composition comprising the Ga containing zeolite and the La modified binder then is prepared by mixing thoroughly zeolite and binder and transformed into a useful shape e.g. into granules, spheres, cylindrical pellets, rings, saddles or star-shaped pellets having a size in the range of about 0.1 mm to about 15 mm, preferred into spheres of 0.5 mm to 5 mm. The weight percentage of binder in the catalyst composition can be between 10 and 90; preferred binder content being 20 to 50 wt. %; most preferred being 30-35 wt. %.

Before exposing the catalyst composition to the lower alkanes under reaction conditions it usually is subjected to pre-treatment steps, e.g. to an oxidation step, optionally a steaming step and to a reduction step. The oxidation step serves to decompose any metals to their oxides and to clean the catalyst surface of moisture and other adsorbed impurities. The reduction step serves to reduce gallium oxide to active gallium species and to disperse the gallium species in the zeolite. Optionally, the catalyst could be subjected to steaming before the reduction step in order to increase thermal/hydrothermal stability of the catalyst, enhance the strength of the catalyst active sites and decrease the coking severity of the catalyst.

The invention further relates to a process for converting lower alkanes into aromatic hydrocarbons using a catalyst composition according to the invention.

Use of this catalyst was found to result in higher lower alkane conversion than other catalyst, not comprising rare-earth metal loaded kaolin as binder.

Processes for converting lower alkanes into aromatic hydrocarbons using a zeolite based catalysts are known per se, e.g. from U.S. Pat. No. 4,855,522. In these processes usually an alkane containing gas stream is fed to a fixed bed of the zeolite catalyst composition. Typical temperatures applied range from 400 to 650° C., preferred being in the range of 500 to 600° C. Pre-treatment of the catalyst composition as mentioned above can be applied when a fixed bed of catalyst composition has been made in the reactor where the conversion reaction will be conducted. Typically applicable Weight Hourly Space Velocity (WHSV) may range from 0.1 to 10 per hour, preferably it ranges from 0.5 to 2.5 per hour.

Lower alkanes and alkenes that can be converted in the reaction according to the invention can have carbon chain length of 1 to 6. Preferred lower alkanes to be converted in the reaction according to the invention are propane and butanes. The aromatic hydrocarbons formed mainly are benzene, toluene and xylenes and are usually denoted as denoted as BTX.

The invention is elucidated by the following examples.

EXPERIMENT 1

Preparation of Ga Containing ZSM-5 Zeolite
(Zeolite A)

0.5714 g gallium nitrate was dissolved in 200 ml demineralised water in a 3-neck round bottom flask. 10 gm of dry ZSM-5 in $NH_4$ form, having a Si/Al ratio of 20 was added. The mixture was heated to 90-95 degrees and stirred at 300 rpm for 24 hours.

The Ga-exchanged ZSM-5 was filtered out and washed with 2 liters of demineralised water. The nominal Ga content of the zeolite was determined by AAS to be 1 wt %.

This procedure can be applied to prepare Ga exchanged ZSM-5 with other Si/Al ratios.

EXPERIMENT 2

Preparation of NH4-GaAlMFI Zeolite (Zeolite B)

50.46 g of sodium trisilicate was added to 200 ml demineralised water in a 500 ml Teflon beaker and stirred vigorously. Separately, a solution of 13.34 g of aluminium nitrate in 50 ml demineralised water, a solution of gallium nitrate in 15 ml demineralised water and a solution of 20.19 g of tetrapropylammonium bromide (TPABr) in 50 ml demineralised water were prepared. The clear solutions of aluminium nitrate, gallium nitrate and TPABr were added slowly one after another to the stirring solution of sodium trisilicate. Further 35 ml water was added at the end. The pH of the mixture was adjusted to 9.0 by adding 1:1 mixture of concentrated $H_2SO_4$ and demineralised water. Vigorous stirring was continued for 30-45 minutes after the pH was adjusted. The mixture was transferred to a 500 ml SS316 autoclave, sealed and heated to 170° C. under constant stirring of 400 rpm for 72 hrs for the crystallization to take place.

The crystalline zeolite was filtered out and washed thoroughly with demineralised water. XRD testing of the dried powder confirmed the MFI framework structure of the zeolite. The zeolite was calcined at 550° C. for 4 hrs in a muffle furnace in flowing dry air. The calcined zeolite was converted to ammonium form by exchanging with 1 M aq. $NH_4NO_3$ solution at 95-98° C. for 4 hrs. The zeolite was characterized by AAS for its Si, Al and Ga content. Zeolite thus prepared is galloaluminosilicate MFI in its ammonium form. The zeolite henceforth will be denoted as $NH_4$—GaAlMFI and had the theoretical Si/Al ratio of 20 and a nominal Ga content of 1.0 wt. %.

EXPERIMENT 3

Preparation of Support Materials (Binders)

1. La Exchanged Kaolin Binder (C-1).

0.187 g Lanthanum nitrate hexahydrate was dissolved in 120 ml demineralised water. 6 Grams kaolin were added. The composition was stirred using magnetic stirrer with heating at 95-98° C. for 24 h in a reflux setup.

The La-exchanged kaolin was filtered. The retained solid was washed with 2 liters of DM water and dried.

The dried La-exchanged kaolin was calcined in a muffle furnace. The kaolin was exposed to a moisture-free air flow of 100 ml/min while being heated at a rate of 8° C. per min, then held at 650° C. for 4 h and cooled to room temperature. A binder material having composition of La/Kaolin (nominal loading of 1 wt. % La on Kaolin) was obtained.

2. Kaolin Binder (C-2)

The calcination process of 1. above was repeated on kaolin without La nitrate exchange.

3. La Modified Al Binder (C-3)

0.187 g lanthanum nitrate was dissolved in 10 ml demineralised water. 6 grams $\alpha\text{-}Al_2O_3$ were added to it to form a slurry, which was stirred under heating to evaporate the water. The paste was dried at 120° C. to give $\alpha\text{-}Al_2O_3$ with a nominal loading of 1 wt. % La.

4. $\alpha\text{-}Al_2O_3$ Binder (C-4)

$\alpha\text{-}Al_2O_3$ as such, without any modification, was selected as binder

EXPERIMENT 4

Preparation of Catalyst Particles

A number of catalyst compositions comprising different zeolite compounds (A or B) and different supports (C-1 to C-4) were prepared in particle form by mixing thoroughly zeolite A or B with one support C in 2:1 ratio. The mixture is pressed at 10 ton pressure to make pellets. The pressed catalyst compositions are crushed, sieved. The fraction containing particles from 0.25 to 0.5 mm and the fraction containing particles from 0.5 to 1.00 mm particles were selected for further use.

EXAMPLE 5 AND COMPARATIVE EXPERIMENTS I, II AND III

Two grams catalyst particles (particle size 0.25-0.5 mm) from each of the combinations AC-1 (according to the invention) and for comparison of AC-2, AC-3 and AC-4 were loaded in a down flow fixed bed microcatalytic reactor and pre-treated in the following way:

Step 1: Exposed for 1 h to moisture-free air flow of 25 ml/min at 630° C.;

Step 2: Exposed for 1 h to 5.0 vol. % steam in 80 ml/min $N_2$ flow at 600° C.;

Step 3: Exposed for 1 h to 25 ml/min hydrogen flow at 500° C.

After the pre-treatment propane is fed to the bed at 34 ml/min. The temperature of the catalyst bed before start of propane flow was 500° C.

The Weight Hourly Space Velocity (WHSV) was 2.0 per hour.

Unconverted propane and formed products were analysed by an on-line Gas Chromatograph, separation column Petrocol DH 50.2, using a Flame Ionization Detector.

The propane conversion obtained with the various catalysts at a temperature of 500° C. is shown in Table 1.

TABLE 1

| | | Propane conversion, % | |
|---|---|---|---|
| Example/Comp. Experiment | Catalyst composition | 15 min on stream | 60 min on stream |
| 5 | AC-1 (Invent.) | 58.8 | 53.8 |
| I | AC-2 (Comp.) | 52.2 | 48.7 |
| II | AC-3 (Comp.) | 52.8 | 49.5 |
| III | AC-4 (Comp.) | 56.7 | 51.3 |

These experiments show the better results in propane conversion of the catalyst composition according to the invention.

Example 6

Catalyst composition particles of 0.25-0.5 mm of combination BC-1 as prepared under Experiment 4 are used for propane conversion.

The experimental set up, reaction and analysing procedure of Example 5 is repeated, with the exception that the pre-treatment step 2 is conducted at 500° C. and 2.0 vol. % steam in 80 ml/min $N_2$ flow.

After 1 hour of reaction at 500° C., the reaction temperature was increased by 20° C. to 520° C. at the rate of 5° C./min and reaction allowed to continue for 1 h. This procedure was repeated until conversion of at least 90% or temperature of 580° C. was reached.

The results are shown in Table 2.

TABLE 2

| Reaction Temp. (° C.) | Time (Min) | Propane Convn. (%) | Product distribution - selectivity (wt. %) | | | |
|---|---|---|---|---|---|---|
| | | | $C_1 + C_2$ | $C_{4+}$ | BTX | $C_{9+}$ aromatics |
| 500 | 60 | 66.3 | 37.4 | 1.0 | 50.4 | 11.2 |
| 520 | 60 | 77.1 | 37.8 | 0.8 | 50.2 | 11.2 |
| 540 | 60 | 83.1 | 38.1 | 0.3 | 50.8 | 10.8 |
| 560 | 60 | 91.5 | 38.0 | 0.0 | 50.0 | 12.0 |

COMPARATIVE EXPERIMENT IV

The procedure of Example 6 was repeated with the catalyst composition BC-2.

The results are shown in Table 3.

TABLE 3

| Reaction Temp. (° C.) | Time (Min) | Propane Convn. (%) | Product distribution - selectivity (wt. %) | | | |
|---|---|---|---|---|---|---|
| | | | $C_1 + C_2$ | $C_{4+}$ | BTX | $C_{9+}$ aromatics |
| 500 | 60 | 50.3 | 33.2 | 3.7 | 53.5 | 9.6 |
| 520 | 60 | 63.5 | 33.9 | 2.1 | 53.2 | 10.9 |
| 540 | 60 | 75.9 | 34.4 | 1.1 | 53.0 | 11.6 |
| 560 | 60 | 86.2 | 33.4 | 0.5 | 51.4 | 14.7 |
| 580 | 60 | 92.4 | 33.0 | 0.3 | 51.1 | 15.6 |

COMPARATIVE EXPERIMENT V

The procedure of Example 6 was repeated with the catalyst composition BC-3.

The results are shown in Table 4.

TABLE 4

| Reaction Temp. (° C.) | Time (Min) | Propane Convn. (%) | Product distribution - selectivity (wt. %) | | | |
|---|---|---|---|---|---|---|
| | | | $C_1 + C_2$ | $C_{4+}$ | BTX | $C_{9+}$ aromatics |
| 500 | 60 | 51.3 | 33.5 | 3.8 | 51.9 | 10.7 |
| 520 | 60 | 63.3 | 34.3 | 2.2 | 51.7 | 11.9 |
| 540 | 60 | 73.2 | 35.5 | 1.3 | 52.3 | 10.9 |
| 560 | 60 | 81.4 | 35.6 | 0.8 | 52.2 | 11.4 |
| 580 | 60 | 85.4 | 35.2 | 0.7 | 50.7 | 13.4 |

COMPARATIVE EXPERIMENT VI

The procedure of Example 6 was repeated with the catalyst composition BC-4. The results are shown in Table 5.

TABLE 5

| Reaction Temp. (° C.) | Time (Min) | Propane Convn. (%) | Product distribution - selectivity (wt. %) | | | |
|---|---|---|---|---|---|---|
| | | | $C_1 + C_2$ | $C_{4+}$ | BTX | $C_{9+}$ aromatics |
| 500 | 60 | 52.8 | 33.2 | 3.3 | 51.3 | 12.2 |
| 520 | 60 | 63.5 | 33.6 | 1.9 | 51.1 | 13.5 |
| 540 | 60 | 72.5 | 34.2 | 1.1 | 50.7 | 14.0 |
| 560 | 60 | 80.7 | 34.1 | 0.4 | 50.8 | 14.7 |
| 580 | 60 | 85.9 | 34.9 | 0.2 | 51.3 | 13.6 |

Example 6 and Comparative Experiments IV to VI show the higher propane conversion of the catalyst composition according to the invention, resulting in a higher BTX yield.

The invention claimed is:
1. A catalyst composition comprising a Ga containing zeolite and a binder, wherein the binder is a La modified kaolin.
2. The catalyst composition according to claim 1, wherein the gallium is present in an amount of at most 0.95 wt % with respect to the total of zeolite and gallium.
3. The catalyst composition according to claim 1, wherein the kaolin has not been acid treated.
4. A process for converting lower alkanes to aromatic hydrocarbons, comprising contacting a feed stream comprising lower alkanes with a catalyst composition comprising a Ga containing zeolite and a binder, wherein the binder is a La modified kaolin, to produce aromatic hydrocarbons.
5. The process according to claim 4 in which the aromatic hydrocarbons consist of at least 45 wt % of benzene, toluene and xylenes.
6. The process according to claim 4, wherein the lower alkanes are C2-C6 alkanes.
7. The process according to of claim 4, wherein the step of contacting a feed stream comprising the lower alkanes with the catalyst composition is at a temperature of 500-600° C.
8. The catalyst composition according to claim 1, wherein the catalyst composition is in a shape that has a size of about 0.1 mm to about 15 mm.
9. The catalyst composition according to claim 1, wherein the catalyst composition is in the shape of spheres having a size of 0.5 mm to 5 mm.
10. The catalyst composition according to claim 1, wherein the amount of Ga on the zeolite is 0.2 to 2.0 wt %.
11. The catalyst composition according to claim 10, wherein the amount of Ga is less than 1 wt %.
12. The process according to claim 4, wherein the catalyst composition comprises 20 wt % to 50 wt % of the binder.
13. The process according to claim 4, wherein the catalyst composition is in a shape that has a size of about 0.1 mm to about 15 mm.
14. The process according to claim 4, wherein the catalyst composition is in the shape of spheres having a size of 0.5 mm to 5 mm.
15. The process according to claim 14, wherein the catalyst composition comprises 20 wt % to 50 wt % of the binder.
16. The process according to claim 4, wherein the kaolin has not been acid treated.
17. The process according to claim 4, wherein the amount of Ga on the zeolite is 0.2 to 2.0 wt %.
18. The process according to claim 17, wherein the amount of Ga is less than 1 wt %.
19. A process for converting lower alkanes to aromatic hydrocarbons, comprising
contacting a feed stream at a temperature of 500-600° C. to produce aromatic hydrocarbons, wherein the feed stream comprises lower alkanes with a catalyst composition comprising a Ga containing zeolite and a binder;
wherein the binder is a La modified kaolin;
wherein the lower alkanes are C2-C6 alkanes.

20. The process according to claim 19, in which the aromatic hydrocarbons consist of at least 45 wt % of benzene, toluene and xylenes.

* * * * *